United States Patent
Mathisen

(10) Patent No.: US 10,709,539 B2
(45) Date of Patent: Jul. 14, 2020

(54) THREE-DIMENSIONAL POLYMERIC MEDICAL IMPLANTS

(71) Applicant: NOVUS SCIENTIFIC AB, Uppsala (SE)

(72) Inventor: Torbjörn Mathisen, Älvsjö (SE)

(73) Assignee: NOVUS SCIENTIFIC AB, Uppsala (SE)

(*) Notice: Subject to any disclaimer, the term of this patent is extended or adjusted under 35 U.S.C. 154(b) by 1185 days.

(21) Appl. No.: 13/756,802

(22) Filed: Feb. 1, 2013

(65) Prior Publication Data

US 2014/0222161 A1    Aug. 7, 2014

(51) Int. Cl.
| | | |
|---|---|---|
| *A61F 2/00* | (2006.01) | |
| *A61L 27/58* | (2006.01) | |
| *A61L 27/56* | (2006.01) | |
| *A61F 2/12* | (2006.01) | |

(52) U.S. Cl.
CPC ............ *A61F 2/0077* (2013.01); *A61L 27/56* (2013.01); *A61L 27/58* (2013.01); *A61F 2/12* (2013.01); *A61F 2002/0086* (2013.01); *A61F 2230/0013* (2013.01); *A61F 2230/0023* (2013.01); *A61F 2230/0045* (2013.01)

(58) Field of Classification Search
CPC .................. A61F 2002/0086; A61F 2/0077
See application file for complete search history.

(56) References Cited

U.S. PATENT DOCUMENTS

| | | | |
|---|---|---|---|
| 3,293,663 A | 12/1966 | Cronin | |
| 4,955,907 A * | 9/1990 | Ledergerber | 623/8 |
| 5,514,181 A * | 5/1996 | Light et al. | 623/13.18 |
| 5,891,558 A | 4/1999 | Bell et al. | |
| 6,162,962 A | 12/2000 | Hinsch et al. | |
| 6,319,264 B1 | 11/2001 | Törmäläet al. | |
| 6,599,323 B2 | 7/2003 | Melican et al. | |
| 8,016,841 B2 | 9/2011 | Magnusson et al. | |
| 8,083,755 B2 | 12/2011 | Mathisen et al. | |
| 2002/0182396 A1* | 12/2002 | DeLucia | A61F 13/495 428/297.4 |
| 2005/0101216 A1 | 5/2005 | Middlesworth et al. | |
| 2005/0288797 A1 | 12/2005 | Howland | |
| 2006/0142786 A1 | 6/2006 | Mathisen et al. | |
| 2010/0318108 A1 | 12/2010 | Datta et al. | |
| 2012/0010636 A1* | 1/2012 | Boey et al. | 606/151 |

FOREIGN PATENT DOCUMENTS

| | | |
|---|---|---|
| JP | 2005-152181 A | 6/2005 |
| WO | WO 94/19029 A1 | 9/1994 |
| WO | WO 02/102592 A1 | 12/2002 |
| WO | WO 2005/118260 A1 | 12/2005 |

OTHER PUBLICATIONS

European Search Report, dated May 2, 2014, 7 pages.
Swedish Office Action, dated Sep. 3, 2013, 6 pages.

\* cited by examiner

*Primary Examiner* — Diane D Yabut

(74) *Attorney, Agent, or Firm* — Foley & Lardner LLP

(57) ABSTRACT

The invention relates to a three-dimensional medical implant, comprising a first thin porous component, and a first load-bearing and volume-creating component, which is connected to the first thin porous component; wherein the load-bearing and volume-creating component comprises an organized structure.

13 Claims, 3 Drawing Sheets

THREE-DIMENSIONAL POLYMERIC MEDICAL IMPLANTS

FIELD OF THE INVENTION

The present invention relates to a three-dimensional resorbable polymeric medical implant, and particularly to a three-dimensional resorbable polymeric medical implant comprising a first porous surface component, a second porous surface component, and a load-bearing and volume-creating component, which is sandwiched between the first porous surface component and the second porous surface component and which comprises an organized open structure, wherein the organized open structure is a formed two-dimensional structure.

BACKGROUND OF THE INVENTION

Three-dimensional medical tissue implants are known. For example, U.S. Pat. No. 5,891,558 to Bell et al. discloses inter alia biopolymer foams as well as biocompatible constructs comprising such biopolymer foams, which can be used in medical implants to replace damaged or diseased tissue, or to provide scaffolds which, when occupied by e.g. host cells, are remodeled to become functional tissue. According to Bell et al. biopolymer foams can be reinforced by winding a biopolymer thread around a foam layer. Further, in U.S. Pat. No. 6,599,323 to Melican et al. it is suggested to reinforce a medical tissue implant, which comprises one or more layers of bioabsorbable polymeric foams, with a preferably bioabsorbable reinforcement component.

For some medical implantation applications—such as scaffolds used predominantly for soft tissue augmentation in breast reconstruction or revision surgery, nipple regeneration, various facial augmentations like chin augmentation, various hernia applications, rhinoplasty and scaffolds used for various tissue engineering purposes where the scaffold is used as a substrate for proliferation of cells ex-vivo or in-vivo or a combination of both—the implant to be introduced into a human or animal body should possess a certain amount of load-bearing capacity without being too rigid, something which otherwise may cause problems during implantation or increased local tissue reactions due to modulus mismatch, especially in soft tissue. Three-dimensional implants where the porosity is higher than 70%, and especially those which are based on or contain a foam-like structure, will—even if reinforced with other structures, components or materials—have a limited ability to withstand compressing forces unless the implant in question is made from stiff materials and thus becomes stiff and non-compliant for most or all soft tissue applications. In unorganized structures such as foams it may also be difficult to control the load-bearing capacity during manufacture of the structures in question. Unorganized porous structures suffer also from varying pore homogeneity, i.e. the porosity is not necessarily the same for all portions of the unorganized structure. Further, in unorganized porous structures, properties like porosity, bending stiffness and compression stiffness are usually strongly related to each other, i.e. in practice it may be difficult to produce a medical implant having a desired porosity and, at the same time, a desired bending or compression stiffness. It is furthermore difficult or impossible to combine different materials and consequently different material properties into a single porous scaffold, which further augment the difficulties and limitations when it comes to design scaffolds with optimal properties for various clinical needs and indications.

SUMMARY OF THE INVENTION

Consequently, there is a need for a three-dimensional resorbable polymeric medical implant having a structure which allows for rapid tissue in-growth in combination with possessing adequate mechanical properties, especially with regard to its ability to withstand compressing forces but still be easily adaptable to underlying tissue structures at the implant site, and whose mechanical properties are predictable, and easily controllable with high enough strengths as required for the specific clinical need. The medical implant should further have a pore homogeneity which is constant throughout the implant structure. Preferably, it should also be possible to provide the medical implant with a specific porosity and at the same time—and more or less independently of the chosen porosity—with a specific bending stiffness (that is, resistance to force applied in a direction perpendicular to the plane of the implant) by combining different materials or by varying the physical shape or morphology within any chosen material.

The above objects are achieved by a three-dimensional resorbable polymeric medical implant described herein.

In one embodiment of the present invention, a three-dimensional resorbable polymeric medical implant is provided, which comprises a porous component and a load-bearing component. The porous component is a substantially two-dimensional structure and is arranged as a layer or sheet. The load-bearing component is arranged on top of the porous component, and is optionally attached to the porous component. The load-bearing component has a height which is larger than the thickness of the porous component, and provides the medical implant with a three-dimensional configuration. The load-bearing component should be strong enough to withstand the compressing forces acting at the implantation site where the medical implant is to be surgically implanted. In accordance with the invention, the load-bearing component therefore comprises an open organized structure, which is a formed two-dimensional structure. The term "formed two-dimensional structure" is defined below. The term "open" means not closed.

In another embodiment of the invention, the medical implant comprises a first porous component, a second porous component, and a load-bearing and volume-creating component, which is arranged between the first porous component and the second porous component such that a sandwiched three-dimensional structure is provided. Also in this embodiment, the load-bearing component comprises an organized structure, which is a formed two-dimensional structure as defined below.

In further embodiments of the present invention, which can comprise two thin porous components, or only one thin porous component, as well as one load-bearing and volume-creating component, the medical implant has a rolled configuration. Other embodiments of the invention include means for controlling the bending stiffness of the present medical implant.

DETAILED DESCRIPTION OF PREFERRED EMBODIMENTS

Figure 1:
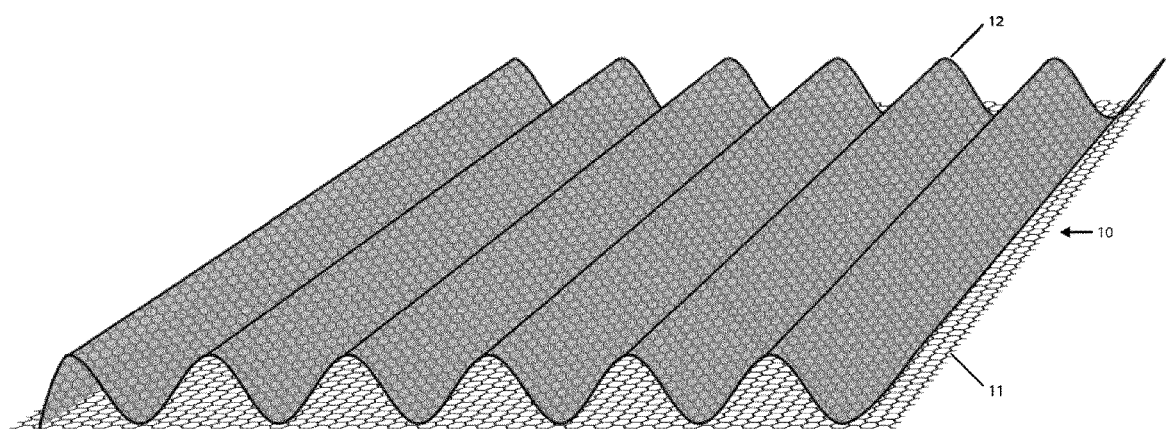
FIG. 1 illustrates schematically a first embodiment of a medical implant according to the present invention, which comprises a thin porous component and a load-bearing and volume-creating component, which has a corrugated shape and is arranged in connection to the thin porous component.

FIG. 1 illustrates schematically a first embodiment of a medical implant 10 according to the present invention. The medical implant 10 comprises a thin porous component 11 and a load-bearing component 12, which in FIG. 1 is arranged on top of the porous component 11 and is connected to the porous component 11. The load-bearing component 12 can be firmly attached, e.g. sewed or tied, to the porous component 11, or be more loosely connected to the porous component 11, e.g. glued or welded, to the porous component 11. The porous component 11 has a limited thickness, approximately 0.02 mm to 1.5 mm thick, and more preferably 0.05 mm to 1.0 mm thick, and can be regarded as a substantially two-dimensional structure and is, for example, arranged as a layer or sheet. Porous components described herein may also be referred to as surface components. The load bearing component 12 is characterized by having both a thickness and a height. The load bearing component 12 is defined as being a flat structure characterized by having a thickness, which is folded or shaped into a three-dimensional structure, which is characterized by having a height. The height of the load bearing component 12 is preferably 2 mm to 15 mm, but more preferably in the range 4 mm to 10 mm, while the thickness of the load bearing component 12 is preferably 0.02 mm to 1.5 mm but more preferably 0.5 mm to 1.0 mm. Thus, the load-bearing component 12 has a height that is more than three (3) times, and preferably more than ten (10) times or even more than hundred (100) times than the thickness of the porous component 11. The load-bearing component 12 therefore provides the medical implant 10 with a three-dimensional configuration, and is therefore also referred to as the load-bearing and volume-creating component 12. Further, the intervals given regarding the thickness of the porous component and thickness and height of the load-bearing and volume-creating component as well as the ratios therebetween apply to all embodiments shown and described herein.

The load-bearing and volume-creating component 12 should be strong enough to withstand the compressing forces that act on the medical implant 10 at the site of implantation. The ability of the load-bearing and volume creating component 12 to withstand compressive strength is, among other things, determined by the choice of material and its morphology, i.e. amorphous or crystalline, the macro and micro design of the load-bearing and volume-creating component as well as the number of attachment points to the porous component 11 and how these have been completed. In the present invention a plurality of factors can be manipulated to achieve the required strength. This is difficult or impossible to achieve in an unorganized structure, such as foam-like or sponge-like structures with porosities higher than 70%. And, if an unorganized structure is provided with a comparable strength to withstand compressing forces, such strength is accompanied by a high bending resistance, i.e. a bending resistance that is too high to be useful or desirable in medical implantation situations since it will impair on the ease of use and limit the surgeon in his/her ability to position the device correctly. When the device is used as a scaffold for vascular or nerve tissue regeneration, the scaffold is most often made as a tube with porous walls being thinner than the diameter of the scaffold. If the bending resistance of such a tube is high, bending will most probably result in kinking or breakage, especially if the material in the scaffold has a high modulus. Therefore and according to the invention, all embodiments of load-bearing and volume-creating components described herein comprise an organized structure, such as a mesh or matrix structure. Herein, the term "organized structure" means that there is a pattern that is intentionally repeated at least twice (and usually many times) in one or more directions. For example, in FIG. 1 a "unit" pattern of one crest and one trough is repeated at regular intervals in the direction from the left to the right in FIG. 1. As will be discussed later in connection with FIG. 10, the organized pattern can be a pattern of crests and troughs (mountains and valleys) that are repeated at regular intervals in two directions. One or more (for example, two, three, four or five) "unit" patterns of predetermined shape (for example, projections, indents, pores, holes, and the like) can be repeated at one or more regular intervals in one or more predetermined directions. The patterns can be formed by, for example, shaping or molding or other techniques. The arrangement can be such that mechanical and physiological properties are the same along two different directions (for example, directions perpendicular to each other) or different. A wide variety of patterns and shapes may be employed, depending on the particular medical application at hand. In an organized structure it is further possible to control the bending resistance without negatively affecting the compression strength, as will be demonstrated below.

As can be seen from FIG. 1, the load-bearing and volume-creating component 12 is arranged as a corrugated mesh, i.e. a flat two-dimensional mesh that has been formed, e.g. annealed, to a corrugated shape, to thereby create a three-dimensional structure. The term "formed two-dimensional structure" is herein defined as a three-dimensional structure which has an originally two-dimensional structure that has undergone a forming process. This is in contrast to, for example, an object made by means of three-dimensional knitting, a process in which, for example, a three-dimensional mesh is produced directly in the knitting process, i.e. without a dedicated forming step. The height of the "formed two-dimensional structure" (for example, in FIG. 1, the vertical distance between the highest point of the crests and the lowest point of the troughs) is substantially larger (for example, by a factor of two, three, five, ten, twenty-five, or fifty or more) than the thickness of the flat two-dimensional mesh from which the "formed two-dimensional structure" is formed.

Figure 2:
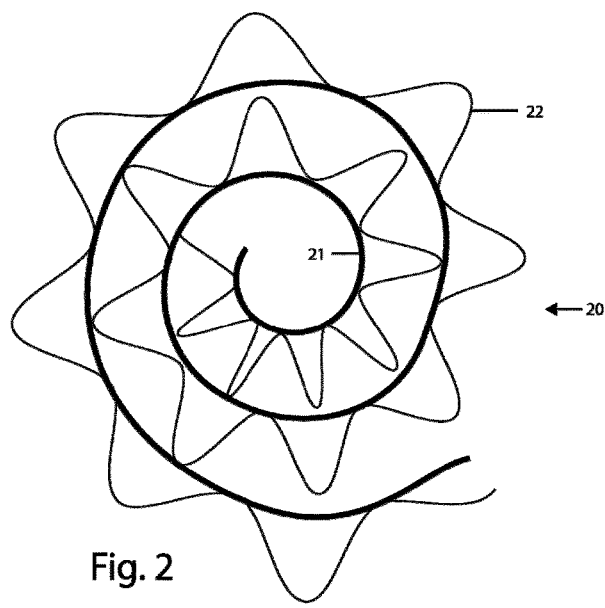
FIG. 2 illustrates schematically a second embodiment of a medical implant according to the present invention, in which a medical implant comprising a thin porous component and a load-bearing and volume-creating component has been given a rolled configuration.

In FIG. 2, a second embodiment of a medical implant according to the present invention is schematically illustrated in cross-section. Here, a medical implant 20, which essentially has the same features as the medical implant 10 described in conjunction with FIG. 1, comprises a thin porous component 21 and a load-bearing and volume-creating component 22, which is connected to the porous component 21. As illustrated in FIG. 2, the medical implant 20 has been given a rolled configuration, and has the shape of spiral, to thereby create a plug for implantation in abnormal bodily orifices, such as fistulas, but more specifically may be used for endogenous tissue engineering purposes within such areas as rhinoplasty, nipple regeneration after mastectomy, reconstructive surgery for cleft palate, regeneration of bone in clavicle fracture and long-bone fractures in combination with extra support. The spiral configuration of medical implant 20 can be obtained in, for example, an annealing process, or the rolled configuration can be achieved by other methods, such as rolling combined with gluing or sewing. According to the invention, all embodiments described herein can be given a rolled configuration.

Figure 3:
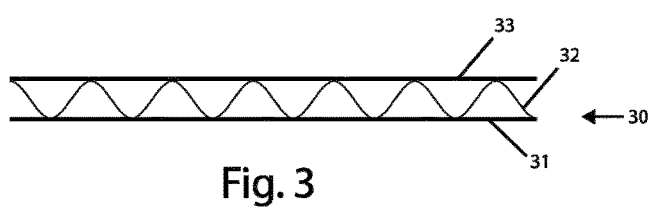
FIG. 3 illustrates schematically a third embodiment of a medical implant according to the present invention, which comprises a first thin porous component, a second thin porous component, and a load-bearing and volume-creating component, which has a corrugated shape and is placed between the first and second thin porous components in a sandwich structure.

FIG. 3 shows a cross-sectional view of a third embodiment of a medical implant 30 according to the present invention, which comprises a first thin porous component 31, a load-bearing and volume-creating component 32, and a second thin porous component 33. The load-bearing and volume-creating component 32 is positioned between the first porous component 31 and the second porous component 33 in a sandwich structure. As described above, the load-bearing component 32 can be connected to the porous components 31, 33 by e.g. sewing, knitting, gluing or welding, but the triple-layer embodiment shown in FIG. 3 provides for further possibilities in that the load-bearing and volume-creating component 32 can be confined and held in place between the first porous component 31 and the second porous component 33, which are connected to each by e.g. sewing, knitting, gluing or welding. In other words, the load-bearing component 32 can be held in place in a flat bag or pouch created by the porous components 31, 33. Thus, the term "connected to" should herein not be interpreted literally, but rather be interpreted as "held in place in close relation to". As can be seen from FIG. 3, the load-bearing and volume-creating component 32 is arranged as a corrugated mesh, i.e. a flat two-dimensional mesh that has been formed, e.g. annealed, to a corrugated shape, to thereby create a three-dimensional structure.

Figure 4:
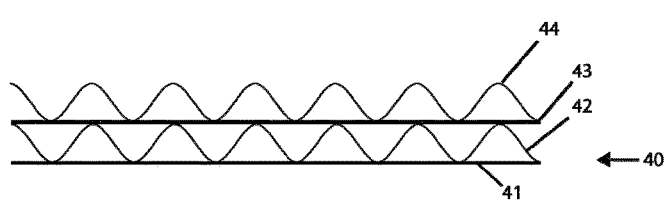
FIG. 4 illustrates schematically a fourth embodiment of a medical implant according to the present invention, which comprises a first thin porous component, a second thin porous component, and a first load-bearing and volume-creating component, which has a corrugated shape and is placed between the first and second thin porous components, and a second load-bearing and volume-creating component, which has a corrugated shape and is arranged in connection to the second thin porous component, such that an aggregate sandwich structure is provided.

FIG. 4 shows a cross-sectional view of a fourth embodiment of a medical implant 40 according to the present invention, which comprises a first thin porous component 41, a first load-bearing and volume-creating component 42, a second thin porous component 43, and a second load-bearing and volume-creating component 44. The first load-bearing and volume-creating component 42 is positioned between the first porous component 41 and the second porous component 43 in a sandwich structure. The second load-bearing and volume-creating component 44 is arranged on top of the second porous component 43 and is connected to the second porous component 43. As discussed above in conjunction with FIG. 3, the first load-bearing and volume-creating component 42 can be connected to the first porous component 41 and/or the second porous component 43 by e.g. sewing, knitting, gluing or welding, or be held in place in a confinement, e.g. a pouch or bag like structure, created by joining together the first porous component 41 and the second porous component 43. The second load-bearing and volume-creating component 44 is connected to the second porous component 43 by sewing, knitting, gluing or welding, or any other suitable technique. As can be seen from FIG. 4, the load-bearing and volume-creating components 42, 44 are arranged as corrugated or otherwise shaped meshes, i.e. flat two-dimensional meshes that have been formed, e.g. annealed, to (but not limited to) corrugated shapes, to thereby create a three-dimensional structure for the medical implant 40.

Figure 5:
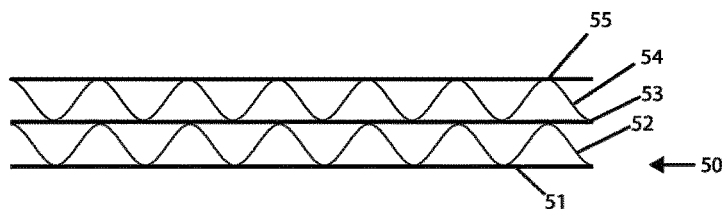
FIG. 5 illustrates schematically a fifth embodiment of a medical implant according to the present invention, which comprises a first thin porous component, a second thin porous component, and a first load-bearing and volume-creating component, which has a corrugated shape and is placed between the first and second thin porous components, and a second load-bearing and volume-creating component, which has a corrugated shape and is arranged in connection to the second thin porous component, and a third thin porous component, which is arranged in connection to the second load-bearing and volume-creating component, such that an aggregate sandwich structure is provided.

FIG. 5 shows a cross-sectional view of a fifth embodiment of a medical implant 50 according to the present invention, which comprises a first thin porous component 51, a first load-bearing and volume-creating component 52, a second thin porous component 53, a second load-bearing and volume-creating component 54, and a third thin porous component 55. The first load-bearing and volume-creating component 52 is positioned between the first porous component 51 and the second porous component 53 in a sandwich structure. The second load-bearing and volume-creating component 54 is arranged on top of the second porous component 53, and the third porous component 55 is arranged on top of the second load-bearing and volume-creating component 54, such the second load-bearing and volume-creating component 53 is connected to both the second porous component 53 and to the third porous component 55, to create an aggregate sandwich structure. As discussed above the term "connected to" should in praxis be interpreted as "held in place in close relation to", which, as also discussed above, in particular applies to the first load-bearing component 52 and the second load-bearing component 54, which can be held in place between the first porous component 51 and the second porous component 53, and between the second porous component 53 and the third porous component 55, respectively, without actually being fixedly attached to any of the porous components. As can be seen from FIG. 5, the load-bearing and volume-creating components 52, 54 are arranged as corrugated meshes, i.e. flat two-dimensional meshes that have been formed, e.g. annealed, to corrugated shapes, to thereby create a three-dimensional structure for the medical implant 50.

Figure 6:
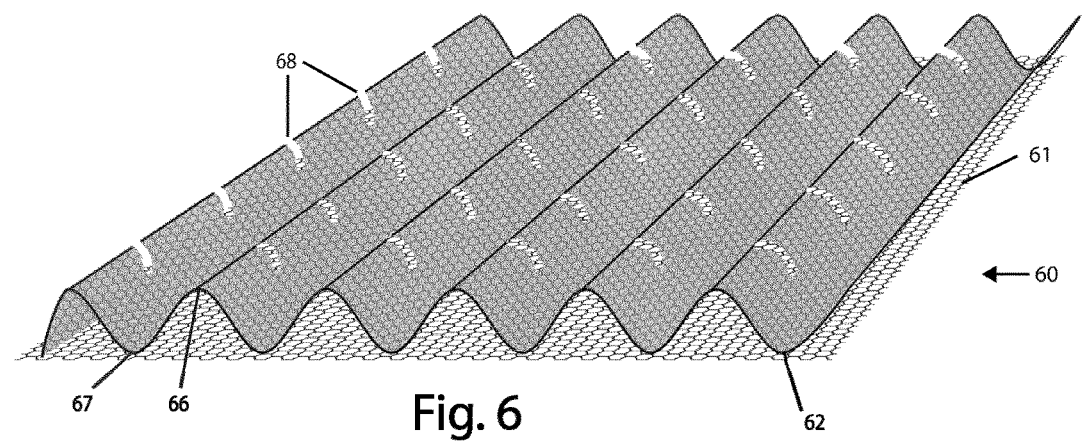
FIG. 6 illustrates schematically a sixth embodiment of a medical implant according to the present invention, which has the features of the embodiment shown in FIG. 1, but additionally provided with cuts, to decrease the bending stiffness of the medical implant in a first direction.

As mentioned above, a particular advantage with the present invention over medical implants comprising unorganized structures, like foams or sponges, is the possibility to influence the bending strength of a medical implant without deteriorating the ability to withstand mechanical compression. In FIG. 6, a first example of how the bending strength (that is, resistance to force applied in a direction perpendicular to the plane of the implant) of a medical implant 60 can be controlled in accordance with the present invention is schematically illustrated. The medical implant 60 is similar to medical implant 10, which was discussed in conjunction with FIG. 1, and comprises a flat thin porous component 61 and a load-bearing and volume-creating component 62, which is connected to the porous component 61. The load-bearing and volume-creating component 62 comprises a corrugated mesh structure, which can have been given its corrugated shape in a dedicated annealing process, such that the load-bearing and volume-creating component 62 comprises a corrugated structure with crests 66 and troughs 67, which herein are commonly referred to as corrugations 66, 67. From FIG. 6 it may be inferred that the bending strength of the implant 60 is higher in the direction perpendicular to the corrugations 66, 67 (for example, when a force is applied perpendicular to the plane of the implant on the back edge of FIG. 6) than in the direction parallel to the corrugations 66, 67 (for example, when a force is applied perpendicular to the plane of the implant on the right-hand edge of FIG. 6). To compensate for this directional difference in bending strength, the crests 66 have been provided with a number of cuts or incisions 68, i.e. material has been removed at a number of positions along the crests 66. By providing such cuts or incisions 68, the mesh implant 60 will bend more easily if a bending force is applied transverse to the crests 66, i.e. the bending strength of the medical implant 60 is decreased in the direction perpendicular to the corrugations 66, 67. Although not shown in FIG. 6, also the troughs 67 can be provided with cuts or incisions. In all embodiments described herein, corrugated structures can be provided with similar cuts or incisions, also when such a corrugated structure is adjoining a thin porous component.

Figure 7:
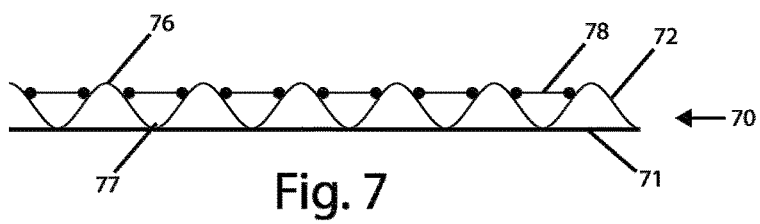
FIG. 7 illustrates schematically a seventh embodiment of a medical implant according to the present invention, which has the features of the embodiment shown in FIG. 1, but additionally provided with extra connections, to increase the bending stiffness of the medical implant in a second direction.

FIG. 7 shows in cross-section another example of how the bending strength of a medical implant 70 can be controlled in accordance with the present invention. The medical implant 70 is similar to medical implant 10, which was discussed in conjunction with FIG. 1, and comprises a flat thin porous component 71 and a load-bearing and volume-creating component 72, which is connected to the porous component 71. The load-bearing and volume-creating component 72 comprises a corrugated mesh structure, which can have been given its corrugated shape in a dedicated annealing process, such that the load-bearing and volume-creating component 72 comprises a corrugated structure with crests 76 and troughs 77, which herein are commonly referred to as corrugations 76, 77. From FIG. 7 it may be inferred that the bending strength of the implant 70 potentially is lower in the direction parallel to the corrugations 76, 77 than in the direction perpendicular to the corrugations 76, 77. To compensate for this directional difference in bending strength, the crests 76 have, at the very top thereof or somewhere along their slopes, been provided with a number of extra connections 78, i.e. adjoining crests 76 have been joined together by threads, fibers or the like, which are sewed, knitted or otherwise attached at a number of positions along the crests 76. (Due to the cross-sectional view of FIG. 7 only one connection 78 is seen in each corrugation 76, 77.) By providing such extra connections 78, the mesh implant 70 will be more resistant to bending if a bending force is applied parallel to the crests 76, i.e. the bending strength of the medical implant 70 has increased in the direction parallel to the extension of the corrugations 76, 77. Although not shown in FIG. 7, also the troughs 77 can be provided with extra connections. In all embodiments described herein, corrugated structures can be provided with similar connections, also when such a corrugated structure is adjoining a thin porous component.

Figure 8:
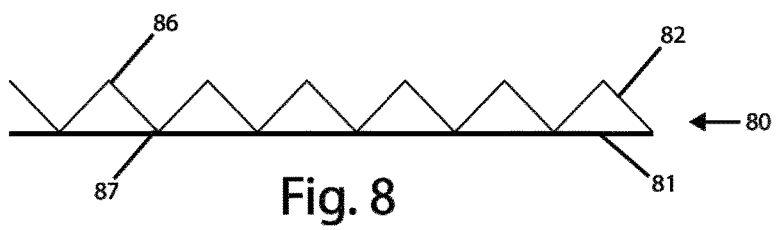
FIG. 8 illustrates schematically an eighth embodiment of a medical implant according to the present invention, which essentially has the features of the embodiment shown in FIG. 1, but wherein a corrugated structure has been given a more triangular cross-section.
Figure 9:
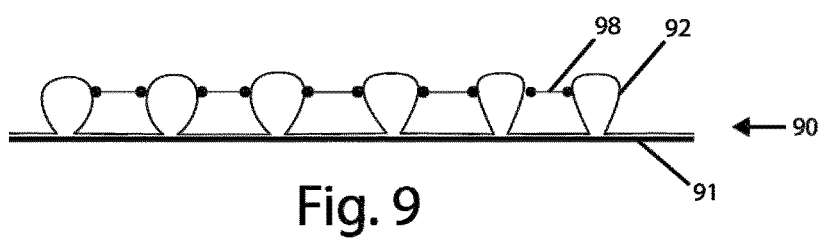
FIG. 9 illustrates schematically a ninth embodiment of a medical implant according to the present invention, which has essentially the features shown in FIG. 7, but wherein a corrugated structure has been given the shape of the Greek letter omega ($\Omega$).

Herein, a corrugated structure means any formed structure that can be achieved in a forming process which forms and converts an essentially two-dimensional structure into a three-dimensional structure. In FIG. 8 and FIG. 9, respectively, two other examples of corrugated structures are disclosed. More specifically, FIG. 8 shows in cross-section a medical implant 80, which comprises a flat thin porous component 81 and a load-bearing and volume-creating component 82, which is connected to the porous component 81. The load-bearing and volume-creating component 82 comprises a corrugated mesh structure, which can have been given its corrugated shape in a dedicated annealing process, such that the load-bearing and volume-creating component 82 comprises a corrugated structure with crests 86 and troughs 87, which herein are commonly referred to as corrugations 86, 87. By comparing, e.g. FIG. 7 and FIG. 8, it can be seen that the corrugations 86, 87 have been given more sharply pointed, triangular shapes as compared to the corrugations 76, 77 of medical implant 70 shown in FIG. 7. Thus, any degree of forming between the rounded corrugations 76, 77 shown in FIG. 7 and the triangular corrugations 86, 87 shown in FIG. 8 is considered to be within the scope of the present invention.

Also other corrugated shapes are possible, and one such example is disclosed in FIG. 9, where a medical implant 90 comprises a flat thin porous component 91 and a load-bearing and volume-creating component 92, which is connected to the porous component 91. As can be seen from FIG. 9, the load-bearing and volume-creating component 92 comprises formed structures, which in cross-section resemble the Greek letter omega or a horseshoe. Herein, also such less "conventional" corrugations are referred to as corrugated structures. The medical implant 90 is further provided with connections 98, which extend between adjoining corrugated structures, to increase the bending stiffness of the medical implant 90 in a direction parallel to its corrugated structures.

Figure 10:
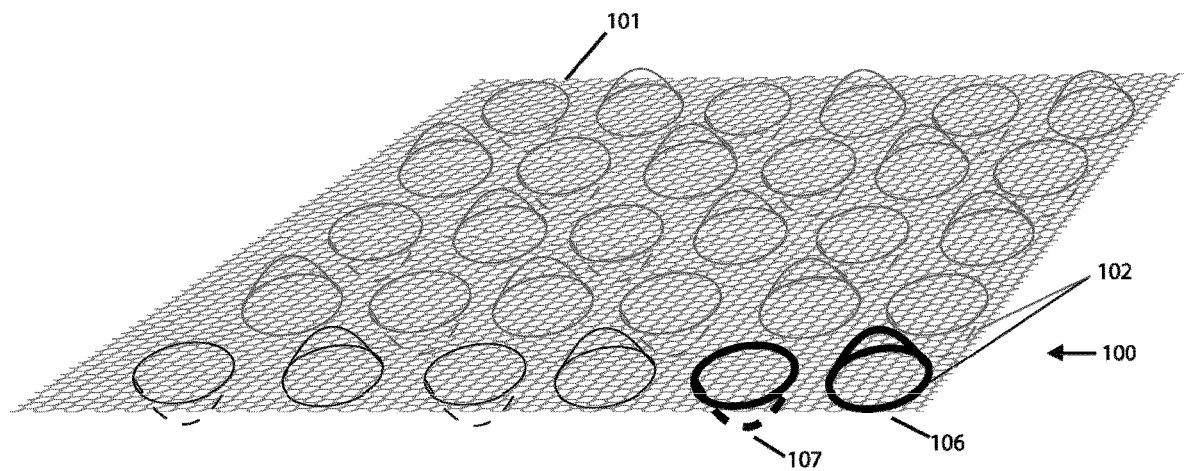
FIG. 10 illustrates schematically a tenth embodiment of a medical implant according to the present invention, which comprises a thin porous component and a load-bearing and volume-creating component, which has a shape comprising elevations and depressions, and is arranged in connection to the thin porous component.

The embodiments of the present invention that were described above in conjunction with FIG. 6 and FIG. 7 as well as FIG. 8 and FIG. 9 can be provided with features (cuts and connections, respectively) that decreases or increases the bending strength in a certain direction, to, for example, create an implant with a more uniform bending strength. A medical implant with, in this respect, uniform mechanical characteristics is illustrated in FIG. 10, where a tenth embodiment of a medical implant 100 according to the present invention is schematically illustrated. The medical implant 100 comprises a flat thin porous component 101 and a load-bearing and volume-creating component 102, which is connected to the porous component 101. The load-bearing and volume-creating component 102 comprises a waffled (or honeycomb) mesh structure, which can have been given its waffled shape in a dedicated thermoforming process such as, but not limited to, an annealing process, such that the load-bearing and volume-creating component 102 comprises a waffled structure with peaks 106 and troughs 107, similar to an egg carton. The troughs 107 can be identical to the peaks 106, except for being inverted, or the peaks 106 and the troughs 107 can have different shapes. And, in particular, waffled structures can exhibit rounded peaks and troughs, or more pointy peaks and troughs. In all embodiments that were described in conjunction with FIG. 1 to FIG. 5, corrugated structures can be replaced with waffled structures (for example, a waffled structure with only peaks or only troughs); and it is also possible to provide a waffled structure with extra connections, e.g. threads or fibers, that extend between and adjoin adjacent peaks (or troughs); and also in waffled structures cuts can be provided to reduce the bending strength of a medical implant.

Figure 11:
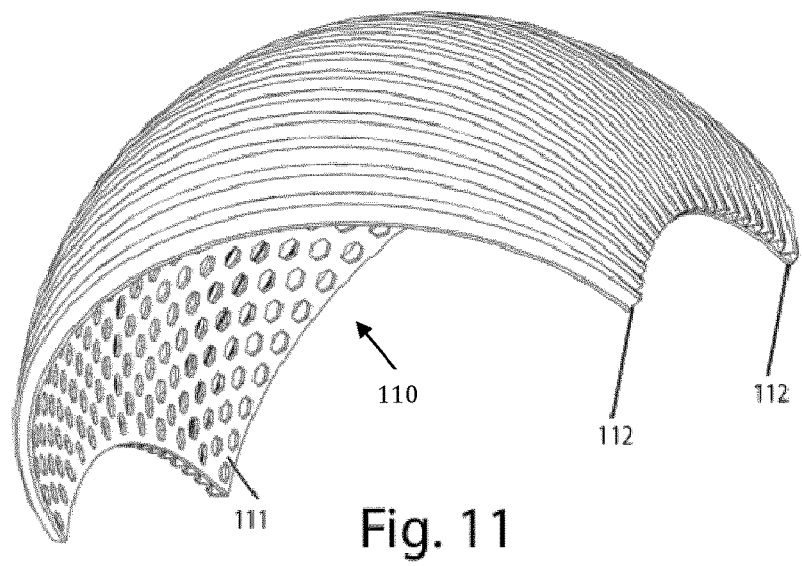
FIG. 11 illustrates schematically an eleventh embodiment of a medical implant according to the present invention, which comprises a thin porous component and a load-bearing component and which has been given a pre-formed, curved shape.

FIG. 11 illustrates an eleventh embodiment of a medical implant 110 according to the present invention, which comprises a thin porous component 111 and a volume-creating component 112. As can be seen in FIG. 11, the medical implant 110 has a curved shape. This curved shape can be provided in, for example, an annealing step in which the medical implant 110 is placed in a correspondingly shaped mould and heat is applied, to give the medical implant 110 a shape that is useful in a particular medical application. Medical implant 110 could for example be used in a medical breast reconstruction procedure. All embodiments presented herein can be pre-shaped to be adapted for a more or less specific clinical application. The term "pre-shaped" refers to forming during manufacturing of a medical implant according to the invention, as opposed to being shaped by a doctor or surgeon during or in immediate connection to the medical procedure at hand.

The embodiments presented herein are characterized by having an embodiment porosity and a component porosity. Both the porous component and the load-bearing component are characterized by having a component porosity, defined as the area of open space relative to the total area, in the range of 10% to 90%, and more preferably in the range of 20% to 70%. Component porosity related to both components is defined as the surface area occupied by open space, i.e. through and through holes or similar, relative the total surface area of the component. Component porosity as defined above can likewise be denoted transparency. The porosity of the embodiment is defined as porosity=$1-d/d_0$, where d is the density of the embodiment, defined as the mass of the embodiment divided by its volume, and $d_0$ is the density of the solid material making up the embodiment. The volume of an embodiment is taken as the volume of the embodiment in question if it had not been composed of porous components; for example the embodiment of FIG. 3 has the volume of a rectangle with the corresponding height, length and width. The embodiment porosity as defined above is above 70% but preferably above 80% and more preferably above 90%. Both components can be made from a variety of techniques like compression molding, injection molding, calendering, extrusion and extrusion with subsequent foil forming, various melt blown and other non-woven techniques also involving electrospinning. Both components can also be made from any combination of the aforementioned techniques. One process technique which is especially suited for the porous component, but also applicable for the load-bearing component, is any type of knitting or weaving techniques, and specifically can circular or flatbed knitting but more preferably warp knitting. There are almost an unlimited number of various knitted structures having different porosity and also homogeneous or anisotropic mechanical properties that can be made by the use of single or multi-bar machines.

Furthermore, the plurality of structures possible by using any of the knitting or weaving techniques above can further be combined with various fibers or yarns having different mechanical properties, which furthermore can be blended, twisted or braided. It is realized that the scaffold described herein can be modified to suit a variety of surgical indications or tissue engineering purposes both ex-vivo and in-vivo. The strength required can be designed into the scaffold by a careful design of the porous component and the load-bearing component, both of which could be made from the same or different materials, and furthermore be realized through the use of different processing technique to fulfill the specified load bearing capacity combined with the ease of bending in one or two dimensions as required.

Both the porous component and the load-bearing component have in themselves a porous structure that can be both regularly or irregularly spread over the respective surface. Anyone component can be made from different materials and also be a laminate of two or more structures being made by two or more different processing techniques. As an example, a thin surface of melt blown fibers or otherwise produced thin non-woven felt can be feed to the knitting machine and used as an inlay in the knitting process or stitched together with any porous component manufactured with any of the above-mentioned techniques. This is especially interesting with non-woven materials made from very thin fibers mimicking the structure of collagen and thus may promote cellular proliferation.

To achieve porosity in a dense non-woven or homogeneous sheet a number of techniques can be used. For example, mechanical punching is probably the easiest technique while more sophisticated techniques include laser technology like carbon dioxide, excimer laser and even femto lasers.

Both the thin porous components as well as all load-bearing and volume-creating components are preferably made from polymeric type of materials and can be inert, partly or fully degradable or dissolvable within the human body. In most situations when partly or fully degradable or dissolvable materials are used, it is desirable that all degradation products or the dissolved components can be absorbed by the surrounding tissue and metabolized or fully excreted not to accumulate inside the body.

Non-limiting examples of inert materials that can be used are polyolefines in various forms, of which specifically polypropylene and polyethylene can be used. A special grade of polyethylene, which normally is referred to as UPMWPE or ultra-high-molecular-weight PE, is particularly well-suited in certain medical applications, and more specifically when the material is present in thin sheets or fiber. Furthermore various types of polyesters such as, but not limited to, polyethylene terephthalate, polypropylene terephthalate, or polybutylene terephthalate can be particular useful.

Non-limiting examples of suitable degradable materials for all thin porous components as well as all load-bearing and volume-creating components described herein are polymers made from the monomers glycolide, lactide and all stereoisomers thereof, trimethylene carbonate, e-caprolactone, dioxanone or dioxepanone, or various combinations thereof. A particularly useful porous component or load-bearing component made from such materials is TIGR® Matrix Surgical Mesh (commercially available from the company Novus Scientific), which is a mesh made from glycolide, lactide and trimethylene carbonate. Any portion of the implant can be made from a resorbable mesh material like the mesh materials described in U.S. Pat. Nos. 8,016,841 and 8,083,755 and U.S. patent application Ser. No. 11/019,534, filed on Dec. 23, 2004. The entire contents of these applications are incorporated herein by reference for the materials, manufacturing processes and other implant features described therein.

Further examples of synthetic degradable polymers that can be used in part or in whole to form the porous components and/or the load-bearing and volume creating components are various aliphatic polyurethanes, such as polyureaurethanes, polyesterurethanes and polycarbonateurethanes, and also materials such as polyphosphazenes, polyorthoesters or various copolymers of β-butyrolactones and ethylene carbonate. Poly-γ-butyrolactone and its various forms as produced in various bacteria(s), naturally occurring or manipulated, is easily transformed into an elastic fiber or thin sheets that can be used in the present invention as is or in combination with any of the aforementioned materials to manufacture the porous or load-bearing or volume creating component.

Natural occurring materials that can be used as porous and load-bearing or volume creating components, include but are not limited to, chitin, chitosan, collagene and silk and even hyalauronic acid, fibroin or fibrinogen when used in combination with any of the above mentioned materials.

Using any of the above mentioned materials in combination with any of the plurality of design methods for the various components as defined above as well as the various techniques, which can be used for joining the components together, leads to a large freedom of choice to purpose design the embodiment to fit in a number of clinical indications requiring varying needs in terms of mechanical properties but also the time period needed for the embodiment to support the tissue structure, temporarily for a short or long time or indefinitely. To achieve the various mechanical requirements needed to support any special tissue or body function, the density of the embodiment should be in the range 0.01 g/cm$^3$ to 0.3 g/cm$^3$, but more preferably in the range 0.01 g/cm$^3$ to 0.15 g/cm$^3$ and more preferably in the range 0.02 g/cm$^3$ to 0.12 g/cm$^3$.

Although the present invention has been described with reference to specific embodiments, also shown in the appended drawings, it will be apparent to those skilled in the art that many variations and modifications can be done within the scope of the invention as described in the specification and defined with reference to the claims below. For example, as suggested in particular by the fourth embodiment shown in FIG. 4 and the fifth embodiment shown in FIG. 5, aggregate medical implants comprising alternating layers of porous components and load-bearing and volume-creating components can according to the invention be made infinitely thick, i.e. the numbers of layers can assume any value, which applies for implants comprising any kind of formed two-dimensional structures, e.g. corrugated or waffled structures.

What is claimed is:

1. A three-dimensional resorbable medical implant, comprising:
    a first thin knitted porous component, and
    a first resorbable load-bearing and volume-creating component, which is connected to the first thin knitted porous component; wherein the resorbable load-bearing and volume-creating component comprises an organized structure,
    wherein a height of the resorbable load-bearing and volume-creating component is more than three times larger than a thickness of the thin knitted porous component,
    wherein the organized structure comprises at least one of
    (1) a corrugated structure having corrugations, the corrugations having a height more than three times larger than the thickness of the thin knitted porous component, or
    (2) a waffled structure, the waffled structure having a height more than three times larger than the thickness of the thin knitted porous component,
    wherein the resorbable load-bearing and volume-creating component is a resorbable two-dimensional structure folded or shaped into a three-dimensional structure such that the height of the resorbable load-bearing and volume-creating component is at least four times larger than a maximum thickness of the resorbable two-dimensional structure to create at least one of the corrugated or waffled structure.

2. A three-dimensional medical implant according to claim 1, wherein the medical implant has a rolled configuration.

3. A three-dimensional medical implant according to claim 1, further comprising a second thin porous component, which is connected to the first resorbable load-bearing and volume-creating component, to create a sandwich structure.

4. A three-dimensional medical implant according to claim 3, further comprising a second load-bearing and volume-creating component, which is connected to the second thin porous component, to create a sandwich structure.

5. A three-dimensional medical implant according to claim 1, wherein the organized structure comprises the at least one corrugated structure, wherein the corrugated structure comprises crests and troughs, and wherein at least one of the crests and/or troughs has at least one cut therein.

6. A three-dimensional medical implant according to claim 1, wherein the organized structure comprises the at least one corrugated structure, wherein the corrugated structure comprises crests and troughs, and wherein at least one pair of adjoining crests or troughs has a connection extending therebetween.

7. A three-dimensional medical implant according to claim 1, wherein the organized structure comprises the at least one waffled structure, wherein the waffled structure comprises peaks and troughs, and wherein at least one of the peaks and/or troughs has at least one cut therein.

8. A three-dimensional medical implant according to claim 1, wherein the organized structure comprises the at least one waffled structure, wherein the waffled structure comprises peaks and troughs, and wherein at least one pair of adjoining peaks or troughs has a connection extending therebetween.

9. A three-dimensional medical implant according to claim 1, wherein the medical implant has been pre-shaped.

10. A three-dimensional medical implant according to claim 1, wherein the first resorbable load-bearing and volume-creating component is porous.

11. A method of manufacturing a three-dimensional resorbable medical implant, comprising:
    forming a resorbable two-dimensional structure into a three-dimensional resorbable load-bearing and volume-creating component such that the resorbable load-bearing and volume-creating component comprises an organized structure; and
    connecting the three-dimensional resorbable load-bearing and volume-creating component to a thin knitted porous component to form a three-dimensional medical implant,
    wherein a height of the three-dimensional resorbable load-bearing and volume-creating component is more than three times larger than a thickness of the thin knitted porous component,
    wherein the organized structure comprises at least one of
    (1) a corrugated structure having corrugations, the corrugations having a height more than three times larger than the thickness of the thin knitted porous component, or
    (2) a waffled structure, the waffled structure having a height more than three times larger than the thickness of the thin knitted porous component,
    wherein the resorbable load-bearing and volume-creating component is the resorbable two-dimensional structure folded or shaped into a three-dimensional structure such that the height of the resorbable load-bearing and volume-creating component is at least four times larger than a maximum thickness of the resorbable two-dimensional structure to create the at least one corrugated or waffled structure.

12. A method of manufacturing a three-dimensional medical implant according to claim 11, wherein the resorbable load-bearing and volume-creating component comprises an organized structure having a predetermined pattern that repeats in one direction.

13. A method of manufacturing a three-dimensional medical implant according to claim 11, wherein the resorbable load-bearing and volume-creating component comprises an organized structure having a predetermined pattern that repeats in two directions.

\* \* \* \* \*